United States Patent [19]
Nakamoto et al.

[11] Patent Number: 4,883,821

[45] Date of Patent: Nov. 28, 1989

[54] AGENT FOR TREATING HYPERURICEMIA

[75] Inventors: Kouji Nakamoto, Saitama; Nobumichi Morishita, Tokyo; Masahide Aoyama, Tokyo, all of Japan

[73] Assignee: Eisai Co., Ltd., Tokyo, Japan

[21] Appl. No.: 332,011

[22] Filed: Mar. 31, 1989

[30] Foreign Application Priority Data

Apr. 13, 1988 [JP] Japan .................................. 63-90890

[51] Int. Cl.$^4$ .......................................... A61K 31/165
[52] U.S. Cl. .................................................... 514/617
[58] Field of Search ............................... 514/649, 617

[56] References Cited

U.S. PATENT DOCUMENTS 4,788,330 11/1988 Nakamoto et al. ................. 562/496

Primary Examiner—Douglas W. Robinson
Assistant Examiner—Raymond J. Henley, III
Attorney, Agent, or Firm—Flynn, Thiel, Boutell & Tanis

[57] ABSTRACT

Hyperuricemia is treated with N-(3-(4'-(2", 6"-dimethylheptyl)phenyl)butanoyl)- ethanolamine.

1 Claim, No Drawings

AGENT FOR TREATING HYPERURICEMIA

The invention relates to a pharmaceutical agent and composition for treating hyperuricemia.

PRIOR ARTS

Although the causes of gout have not been completely clarified, it is believed that hyperuricemia is caused by accumulation of uric acid in the body by excessive production or lowering of excretion of uric acid.

Accordingly, when it is intended to treat gout with a medicine, administration of a medicine having a function of lowering the uric acid level in serum is a main means.

Gout is one of the incurable diseases, and control of the uric acid level should be continued for life. Accordingly, it is important that a medicine having a low adverse effect should be used in an amount as small as possible.

Allopurinol, benzbromarone and probenecid have been clinically used, but they have various adverse effects and are not satisfactory.

For example, allopurinol which is believed to inhibit formation of uric acid in the final stage or purine metabolism causes efflorescence, gastrointestinal disorders, liver troubles and hematogenic organ troubles and involves a risk of having bad influences on other metabolic systems. Accordingly, care should be taken when allopurinol is continuously administered for a long time.

Under this circumstance, development of a medicine for the treatment of gout having a function of lowering the uric acid level safely without any adverse effect is eagerly desired.

(Summary of the invention)

Under these circumstances, we have made researches with a view of developing a compound having a function of lowering the uric acid level and also having a high safety and, as the result, have found that this object can be attained by using N-{3-[4'-(2",6"-dimethylheptyl)phenyl]butanoyl}ethanolamine represented by the following chemical structural formula:

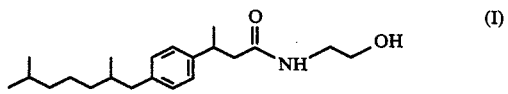

(I)

We have now completed the present invention based on this finding.

The invention provides a method for treating hyperuricemia, which comprising administering a pharmacologically effective amount of N-(3-(4'-(2",6"-dimethylheptyl)phenyl)butanoyl)ethanolamine to a patient; use of the same compound for manufacturing a medicine to treat hyperuricemia; an agent for ameliorating hyperuricemia, which comprises the same compound; and a pharmaceutical composition which comprises a pharmacologically effective amount of the same compound and a pharmacologically acceptable carrier.

The compound of the invention serves to improve hyperuricemia and lower the uric acid level.

The ethanolamine derivative represented by the above-mentioned structural formula (I) is a compound disclosed in Japanese Patent Laid-Open No. 210050/1986 and has an anticholesterolemic action. To our surprise, we have now found that the compound has a function of reducing the uric acid level in serum.

N-{3-[4'-(2",6"-Dimethylheptyl)phenyl]butanoyl}-ethanolamine used in the present invention can be prepared, for example, according to the process disclosed in Example 20 of the above-mentioned laid-open patent.

The physical and chemical properties of the compound are as follows.

Molecular Formula: $C_{21}H_{35}NO_2$.
Molecular Weight: 333.
Structural Formula:

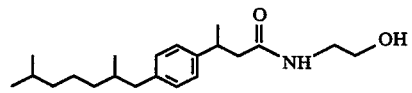

Properties:
The compound is a white to light yellow waxy or crystalline solid and is sometimes a liquid, and the compound has no smell.

Melting Point:
35° to 45° C. (as determined by thermal analysis)

Solubility:
Highly soluble in anhydrous ethanol, ethyl acetate, ethanol, chloroform, acetonitrile and n-hexane but substantially insoluble in water.

A production example of the compound of the present invention will now be described as a referential example.

REFERENTIAL EXAMPLE (PRODUCTION EXAMPLE)

Synthesis of N-{3-[4'-(2",6"-dimethylheptyl)phenyl]butanoyl}ethanolamine

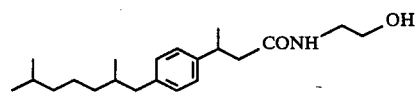

In 10 ml of tetrahydrofuran was dissolved 29.0 g of 3-[4'-(2",6"-dimethylheptyl)phenyl]butyric acid, and 25.3 g of triethylamine was added to the solution. 13.0 g of ethyl chlorocarbonate was added dropwise to the mixture under ice cooling.

After termination of the reaction, the reaction mixture was added to 100 ml of a solution of 9.0 g of ethanolamine in tetrahydrofuran at a temperature lower than 0° C.

The reaction mixture was poured into water, neutralized with dilute hydrochloric acid and extracted with ether. The extract was washed with water, concentrated and purified by silica gel column chromatography to obtain 29.1 g (yield: 87.4%) of the intended compound (in the form of a colorless oil).

| Elementary analysis values as $C_{21}H_{35}NO_2$: | | |
| --- | --- | --- |
|  | C | H |
| calculated (%) | 75.63 | 10.58 |
| found (%) | 75.78 | 10.64 |

Mass (m/z): 333 (M+).
$^1$H-NMR (CDCl$_3$) δ: 0.84(3H, d, J=7 Hz), 0.86(6H, d, J=7 Hz), 0.9~1.9(8H), 1.28(3H, d, J=8 Hz), 2.1~2.8(4H, m), 30–3.4(3H), 3.4–3.6(2H), 6.6~6.9(1H), 7.0–7.2(4H).

In order to clarify the effect of the present invention, the results of the phase I clinical test conducted on men will now be described.

CLINICAL TEST EXAMPLE (Method)

Capsules containing 300 mg of the compound of the present invention, N-{3-[4''-(2'',6''-dimethylheptyl)-phenyl]butanoyl}ethanolamine, were administered to 5 healthy adult men for 7 days three times per day after meals. For comparison, a placebo was administered to two other healthy adult men. Thus, the phase I clinical test was conducted.

On the first, fourth and sixth days after the start of the administration, blood was sampled in the morning before the administration, and the uric acid level in serum was measured according to a customary method (enzymatic method). With respect to the measured values, the significance test was conducted between the group to which the compound of the present invention was administered and the group to which the placebo was administered.

(Results)

The obtained results are shown in Table 1.

TABLE 1

| Administered medicine | Healthy man | 1st day | 4th day | 6th day | 8th day | 11th day |
|---|---|---|---|---|---|---|
| compound | A | 4.9 | 8.5 | 3.0 | 3.2 | 4.8 |
| of present | B | 6.4 | 2.9 | 2.6 | 3.1 | 5.6 |
| invention | C | 5.9 | 2.6 | 2.4 | 3.1 | 7.2 |
|  | D | 7.0 | 3.6 | 3.2 | 4.0 | 5.3 |
|  | E | 4.7 | 2.8 | 2.5 | 2.7 | 4.8 |
|  | average | 5.8 | 3.1* | 2.7* | 3.2* | 5.5 |
| placebo | H | 6.7 | 6.7 | 6.4 | 6.7 | 8.1 |
|  | G | 5.2 | 4.7 | 4.9 | 4.8 | 6.1 |
|  | average | 6.0 | 5.7 | 5.7 | 5.8 | 7.1 |

Note
*p < 100

In the above table, each value indicates the uric acid level (mg/dl) in serum, and A through G in the column of "Healthy man" represent the adult men to whom the medicine was administered.

The table shows the following facts.

In the group to which the compound of the present invention was administered, on the fourth day, significant lowering in the uric acid level in serum was observed and then an equilibrium state was maintained in the vicinity of the normal reference value. However, the uric acid level was promptly elevated to the value before the start of the administration if the administration was stopped, and accumulation of the medicinal effect was not observed.

The results of the acute toxicity test of the compound of the present invention will now be described.

ACUTE TOXICITY TEST

The acute toxicity test was carried out by oral, intraperitoneal and subcutaneous administration to 7- to 8-week old Sic-SD rats and Slc:ICr mice. The $LD_{50}$ values are collectively shown in Table 2. The case of death was observed within 5 days from the start of the administration.

TABLE 2

| | $LD_{50}$ Values of Rats and Mice | | | |
|---|---|---|---|---|
| | Rats | | Mice | |
| Course | male | female | male | female |
| oral | 4260 mg/kg | 1910 mg/kg | >2560 mg/kg | 4581 mg/kg |
| intraperitoneal | 1340 mg/kg | 572 mg/kg | 792 mg/kg | 737 mg/kg |
| subcutaneous | >8000 mg/kg | 6351 mg/kg | >5000 mg/kg | >5000 mg/kg |

From the foregoing test examples, it can be seen that the compound of the present invention has an excellent function of reducing the uric acid level in serum, and therefore the compound of the present invention is effective in ameliorating and treating hyperuricemia.

More specifically, the compound of the present invention is effective in treating gout by ameliorating and treating hyperuricemia. This disease often accompanies hypertension, arteriosclerosis and myocardial infraction because of characteristics of the disease. Accordingly, the compound of the present invention is effective in treating hypertension, arteriosclerosis or myocardial infraction accompanied by hyperuricemia.

When the compound of the present invention is to be administered to a patient suffering from hyperuricemia, the dose greatly differs according to the kind of the patient, the extent of disease and the age of the patient, but it is preferred to administer the compound of the present invention in an amount of about 10 to 2,000 mg, especially about 10 to 1,000 mg, particularly especially 50 to 600 mg, per day, 2 to 4 times a day, orally or parenterally. The compound of the present invention is administered in the form of powder, fine granule, granule, tablet, capsule or injection. These medicines are prepared according to customary procedures using ordinary pharmaceutical carriers.

For example, a solid medicine for oral administration is prepared by adding an excipient and, if necessary, binder, disintegrating agent, lubricant, colorant and corrigent to the main ingredient, and forming the mixture into tablet, coated tablet, granule, powder or capsule.

As the excipient, there can be mentioned lactose, corn starch, white sugar, glucose, sorbitol, crystalline cellulose and silicon dioxide. As the binder, there can be mentioned polyvinyl alcohol, polyvinyl ether, ethylcellulose, methylcelulose, gum arabic, tragacanth, gelatin, shellac, hydroxypropylcellulose, hydroxypropylstarch and polyvinylpyrrolidone. As the disintegrating agent, there can be mentioned starch, agar, gelatin powder, crystalline cellulose, calcium carbonate, sodium hydrogencarbonate, calcium citrate, dextrin and pectin. As the lubricant, there can be mentioned magnesium stearate, talc, polyethylene glycol, silica and hardened vegetable oil. A colorant, addition of which to a medicine is allowed, can be used. As the corrigent, there can be used cocoa powder, menthol, aromatic powder, peppermint oil, borneol and cinnamon powder. Tablets and granules may be coated with sugar or gelatin according to need.

In preparing an injection, pH adjusting agent, buffer agent, stabilizer, solubilizing agent and the like are added to the main ingredient according to need, and the mixture is formed into a subcutaneous, intramuscular or intravenous inejction according to customary procedures.

An example of the preparation of a tablet as a medicine comprising the compound of the present invention, N-{3-[4′-(2″,6″-dimethylheptyl)phenyl]butanoyl}ethanolamine (active ingredient), will now be described.

PREPARATION EXAMPLE (TABLET)

| | |
|---|---|
| active ingredient | 10 g |
| anhydrous silicic acid | 50 g |
| crystalline cellulose | 70 g |
| corn starch | 36 g |
| hydroxypropylcellulose | 10 g |
| magnesium stearate | 4 g |

By using the above components, tablets (each tablet containing 180 mg of the above composition) were prepared according to customary procedures.

We claim:

1. A method for treating hyperuricemia, which comprises administering to a patient in need thereof, a pharmacologically effective amount of N-(3-(4′-(2″,6″-dimethylheptyl)phenyl)butanoyl)ethanolamine.

* * * * *